US005348945A

United States Patent [19]

Berberian et al.

[11] Patent Number: 5,348,945

[45] Date of Patent: Sep. 20, 1994

[54] METHOD OF TREATMENT WITH HSP70

[75] Inventors: Paul A. Berberian; Michael Tytell, both of Winston-Salem, N.C.; David J. Gower, Oklahoma City, Okla.

[73] Assignee: Wake Forest University, Winston-Salem, N.C.

[21] Appl. No.: 76,279

[22] Filed: Jun. 11, 1993

Related U.S. Application Data

[63] Continuation of Ser. No. 680,209, Apr. 4, 1991, abandoned, which is a continuation-in-part of Ser. No. 505,934, Apr. 6, 1990, abandoned.

[51] Int. Cl.[5] .............................................. A61K 37/02
[52] U.S. Cl. ........................................ 514/21; 514/12
[58] Field of Search .................................. 514/12, 21

[56] References Cited

FOREIGN PATENT DOCUMENTS

WO89/12455 9/1989 PCT Int'l Appl. .
WO90/02564 3/1990 PCT Int'l Appl. .

OTHER PUBLICATIONS

Tytell et al, Adv. in Neurology, vol. 59, edited by Frederick J. Seil, Raven Press, Ltd., NY 1993, pp. 293–303.
Tytell et al, Transactions of the Amer. Soc. for Neurochem. (1994) Abstract.
Smith et al, Biological Bulletin, vol. 185: 293–294 (1993).
Johnson et al, Experimental & Molecular Pathology, 58: 155–168 (1993).
Widnell et al, Essenhal Cell Biology, (1990) pp. 116–130.
P. Berberian, Ph.D., *Stress Protein in Plaque: Troublemaker or Troubleshooter?,* American Heart Association's Sixteenth Science Writers Forum, Monterey, Calif., Jan. 15–18, 1989.
M. Barbe et al., "Hyperthermia Protects Against Light Damage in the Rat Retina," *Science* 241, 1817 (1988).
P. Berberian et al., "Exogenous 70 Kd Heat Shock Protein Increases Survival of Arterial Cells from Normal and Atherosclerotic Aortas," *Arteriosclerosis* 9, No. 5, 726a (1989).
P. Berberian et al., "Update: Heat Shock Protein and Arterial Cell Death," The Stroke Monitor, p. 1 (Spring 1989).
H. Chiang et al., "A Role for a 70-Kilodalton Heat Shock Protein in Lysosomal Degradation of Intracellular Proteins," *Science* 246, 382 (1989).
M. Chopp et al., "Heat Shock and Thermotolerance in Early Rat Embryo Development," *Neurology* 39, 1396 (1989).
M. Chopp et al., "Reduction of Hyperthermic Ischemic Acidosis by a Conditioning Event in Cats," *Stroke* 20, No. 10, 1357–1360 (Oct. 1989).
L. Hightower and P. Guidon, "Selective Release from Cultured Mammalian Cells of Heat-Shock Proteins," *J. Cell. Physiol.* 138, 257 (1989).
H. Pelham, "Heat Shock and the Sorting of Luminal ER Proteins," *EMBO Journal* 8, No. 11, 3171 (1989).
S. Tomosovic and D. Welsh, "Heat Stress Proteins and Experimental Cancer Metastasis," *Int. J. Hyperthermia* 2, No. 3, 253 (1986).
D. Walsh et al., "Heat Shock and Thermotolerance During Early Rat Embryo Development," *Teratology* 36, 181–191 (1987).

(List continued on next page.)

*Primary Examiner*—Michael G. Wityshyn
*Assistant Examiner*—Choon P. Koh
*Attorney, Agent, or Firm*—Bell Seltzer Park & Gibson

[57] ABSTRACT

A method of combating mortality in a cell or tissue under stress is disclosed. The method comprises contacting hsp70 to the cell or tissue in an amount effective to enhance the survival of that cell or tissue. The method may be employed in the combating of atherosclerosis, restenosis after angioplasty, and nerve damage in human or animal subjects in need of such treatment. A pharmaceutical composition comprising a therapeutically effective amount of hsp70 in a pharmaceutically acceptable formulation is also disclosed.

32 Claims, No Drawings

OTHER PUBLICATIONS

D. Walsh et al., "Regulation of the Inducible Heat Shock 71 Genes in Early Neural Development of Cultured Rat Embryos," *Teratology* 40, 321–334 (1989).

R. Allen et al., "A Novel hsp70-Like Protein (P70) is Present in Mouse Spermatogenic Cells," *Mol. Cell. Biol.* 8, 828 (1988).

P. Berberian et al., "Exogenous 70 Kd Heat Shock Protein Increases Survival of Normal and Atheromatous Arterial Cells," *FASEB J.* 4, A1031 (1990).

V. Guerriero et al., "HSP70-Related Proteins in Bovine Skeletal Muscle," *J. Cell. Physiol.* 140, 471 (1989).

T. Hatayama et al., "Separation of Rat Liver HSP70 & HSP71 by High Performance Liquid Chromatography with a Hydroxylapatite Column," *J. Chromatog.* 481, 403 (1989).

A. Johnson et al., "Time-Correlated Cytoprotection by 70kD Heat Shock Protein in Arterial Cells During Metabolic Stress," *FASEB J.* 4, A1032 (1990).

A. Johnson et al., "Effect of Heat Shock Proteins on Survival of Isolated Aortic Cells from Normal and Atherosclerotic Cynomolgus Macaques," *Atherosclerosis* 84, 111 (1990).

D. Macejak et al., "Isolation and Characterization of Human HSP70 Expressed in *Escherichia coli*," *Arch. Biochem. Biophys.* 280, 53 (1990).

N. Mivechi et al., "Effects of Heat Shock Proteins (Mr 70,000) on Protein and DNA Synthesis at Elevated Temperatures in vitro," *Cancer Res.* 49, 1492 (1989).

METHOD OF TREATMENT WITH HSP70

This application is a continuation of application Ser. No. 07/680,209, filed 4, Apr. 1991, now abandoned, which is a continuation-in-part of-co-pending application Ser. No. 07/505,934, filed Apr. 6, 1990, now abandoned.

FIELD OF THE INVENTION

The present invention relates to methods of enhancing the survivability of cells and tissues by treating the same with exogenous hsp70.

BACKGROUND OF THE INVENTION

Heat shock proteins (hsps) are highly conserved constitutive and induced proteins found in cells from bacteria to human beings. S. Lindquist, *Ann. Rev. Biochem* 55, 1151 (1986). The constitutive hsps are critical to many diverse cellular functions. The most ubiquitous and best studied hsp family, the group of hsp's with molecular weights close to 70,000 daltons (hsp70), has been shown to assist in translocation of proteins into the endoplasmic reticulum and mitochondria, R. Deshais et al., *Nature* 332,800 (1988), W. Chirico et al., *Nature* 332, 805 (1988). Hsp 70 also has been implicated as the clathrin-uncoating ATPase, T. Chapell et al., *Cell* 45, 3 (1986). Potential structural functions of other hsps include: linking the actin cytoskeleton to the plasmalemma, S. Koyasu et al., *Proc. Natl. Acad. Sci. USA* 83, 8054 (1986); specifically binding saturated fatty acids, P. Guidon and L. Hightower, *Biochemistry* 25, 3231 (1986); P. Guidon and L. Hightower, *J. Cell Physiol.* 128, 239 (1986), and as components of some steroid binding receptors. E. Baulieu and M. Catelli, *Alan. R. Liss, Inc., New York*, 275 (1989). These proteins also appear to act as antigens in anti-bacterial, D. Young et al., *Proc. Natl. Acad. Sci. USA* 85, 4267 (1988); A. Mehlert et al., *Biochem. Soc. Trans.* 16, 721 (1988), and autoimmune reactions. S. Minota et al., *J. Exp. Med.* 168, 1475 (1988), S. Minota et al., *J. Clin. Invest.* 81, 106 (1988). Several other functions have been suggested as well. *See* S. Lindquist, *Ann. Rev. Biochem* 55, 1151 (1986), M. Schlesinger et al., Cold Spring Harbor Laboratory, 1982, M. Pardue et al., Alan R. Liss, Inc. (1989), M. Schlesinger, *J. Cell Biol.* 103, 321 (1986), E. Craig, *CRC Critical Reviews in Biochemistry, Vol.* 18, *no.* 3, 239 (1985).

The inducible forms of hsps are elicited by a variety of stressors, including elevated temperature, M. Schlesinger et al., Cold Spring Harbor Laboratory, 1982, heavy metals, M. Schlesinger et al., *Alan R. Liss, Inc.*, 137 (1989), amino acid analogs, P. Kelley and M. Schlesinger, *Cell* 15, 1277 (1978), L. Hightower, *J. Cell. Physiol.* 102, 407 (1980), oxidative radicals, M. Ashburner, *Chromosoma* 31, 356 (1970), J. Compton and B. McCarthy, *Cell* 14, 191 (1978) ischemia or return from anoxia, S. Guttman, *Cell* 22, 299 (1980), M. Ashburner and J. Bonner, *Cell* 17, 241 (1979), mechanical trauma, L. Hightower and F. White, Cold Spring Harbor Laboratory, 369 (1982), D. Gower et al., *J. Cell Biol.* 103, 291 (1986), and abnormal proteins. J. Ananthan et al., *Science* 232, 522 (1986). The unifying functional characteristic is that they act to maintain normal cellular function under non-ideal conditions.

The functional importance of hsps to cells under stress extends to the arterial wall and atherosclerosis. The developing plaque involves histological and biochemical changes in the composition of the arterial wall, R. Ross, *N. Eng. J. Med.* 314, 488 (1986). In chronically stressed atherosclerotic plaque cells, hsp alterations may have serious implications. As an example, one general effect of hsps is to stabilize membranes of cells, R. Shiver et al., *Eur. J. Cell Biol.* 46, 181 (1988), and it has been suggested that stabilization of arterial lysosomal membranes may facilitate plaque cells to entrap lipids, J. Berthet et al., *Biochem. J.* 59, 182 (1951), C. deDuve, *Harvey Lectures* 59, 49 (1965), P. Berberian et al., *Fed. Proc.* 43, 711 (1984). Cell stabilization by hsps additionally may help to determine the relative survival of cells within various regions of the developing plaque, while its relative deficiency may define areas vulnerable to necrosis.

There is evidence that hsps can be exchanged between cells. L. Hightower and P. Guidon, *J. Cell. Physiol.* 138, 257 (1989), M. Tytell et al., *Brain Res.* 363, 161 (1986). Thus, it is possible that hsps' effects may not be limited to the stressed cell synthesizing them. However, no one has tested the effect of exogenously added hsps on cell survival. The present invention is based on our findings after undertaking such tests.

SUMMARY OF THE INVENTION

A first aspect of the present invention is a method of combating mortality in a cell under stress. The method comprises contacting hsp70 to the cell in an amount effective to enhance the survival of that cell.

A second aspect of the present invention is a method of combating mortality in a tissue under stress, such as arterial tissue. The method comprises contacting hsp70 to the tissue in an amount effective to enhance the survival of cells residing in that tissue. The tissue may be treated in vivo or in vitro. Among other things, this method is useful for preserving organs for transplant.

A third aspect of the present invention is a method of combating atherosclerosis in a human or animal subject in need of such treatment. The method comprises administering the subject hsp70 in an amount effective to reduce necrosis in arterial plaques residing in the subject.

A fourth aspect of the present invention is a method of combating arterial restenosis after angioplasty in a human or animal subject in need of such treatment comprising administering arterial tissue residing in the subject in need of such treatment hsp70 in a restenosis-combating amount.

A fifth aspect of the present invention is a method of combating nerve damage in a human or animal subject in need of such treatment, comprising administering the subject hsp70 in an amount effective to enhance the survival of nerve cells under stress.

A sixth aspect of the present invention is a pharmaceutical composition comprising a therapeutically effective amount of hsp70 in a pharmaceutically acceptable formulation.

A seventh aspect of the present invention is the use of hsp70 for the preparation of a pharmaceutical formulation for the combating of mortality in arterial tissue.

An eighth aspect of the present invention is the use of hsp70 for the preparation of a pharmaceutical formulation for the combating of mortality in nerve tissue.

DETAILED DESCRIPTION OF THE INVENTION

Cells of any origin may be treated by the method of the present invention, including animal, plant, and bacterial cells. Cells may be treated in vitro or in vivo.

Likewise, tissues of any origin, including animal and plant tissue, may be treated by the method of the present invention either in vitro or in vivo. Animal cells and tissues are preferred for carrying out the present invention, with mammalian (e.g., dog, cat, human) cells and tissue particularly preferred. The term "animal" as used herein, refers to the subjects of veterinary medicine, such as dog, cat, cow, pig, and horse.

Cells and tissue which are under stress are treated with hsp70 to combat mortality. For example, cells which are maintained in culture (e.g., for the purpose of producing proteins or other materials from the cells) or tissue which is maintained in culture (e.g., complete organs such as heart, lung, liver or kidney prior to transplant) may be considered as "under stress" for the purpose of practicing the present invention. For example, organs could be immersed in a solution containing HSP70, or a larger organ perfused through its vasculature, with an HSP70 solution. The HSP70 would be taken up by the cells of the organ, making them more resistant to the lack of blood, nutrients and other needed substances that exists once they are removed from the body. Likewise, the HSP70 could be included in a reperfusion solution to combat tissue reperfusion injury. The HSP70 may be added to known solutions and used in accordance with procedures known to those skilled in the art for these purposes. Such solutions and procedures are disclosed in U.S. Pat. No. 4,920,044, titled "Intracellular Flush Solution for Preserving Organs", U.S. Pat. No. 4,879,283 titled "Solutions for the Preservation of Organs", U.S. Pat. No. 4,873,230 titled "Composition for the Preservation of Organs", and U.S Pat. No. 4,798,824 titled "Perfusate for the Preservation of Organs". Applicants intend the disclosures of these and all other patents cited herein to be incorporated herein by reference.

Tissue under stress in vivo may also be treated. For example, arterial and myocardial tissue may be treated by administering hsp70 during by-pass surgery to enhance the survivability of cells in that tissue. Cardiac ischemia may be treated by administering hsp70 about the time of myocardial infarction to enhance the survivability of cells in those tissues. The kidney may be protected from damage from toxic substances such as the antibiotic Gentamicin by the administration of hsp70. Arterial tissue may be administered hsp70 during laser angioplasty and atherectomy to reduce damage to these tissues arising from such procedures.

Nerve tissue (i.e., peripheral nerve and central nerve) which is under stress in vivo may also be treated by the method of the present invention. For example, peripheral nerves which are severed are subject to retrograde degeneration, which degeneration may culminate in death of the nerve cell, or soma, if too great a portion of the nerve's axon is distal to the site of the cut. If degeneration does not culminate in cell death, then an opportunity exists for the nerve to regenerate. Thus, hsp70 may be administered to such nerve tissue, through administration to the host animal, to combat cell mortality which may result from the severing of the peripheral nerve.

Nerve tissue may also be subject to anoxic stress in vivo. For example, anoxic stress may arise from a stroke or burst aneurism which damages nerve tissue by depriving the tissue of blood. When central nerve tissue is so damaged, the damage typically occurs in a watershed pattern in relation to the blood vessels: tissue closest the damaged supply vessel is most severely damaged; tissue furthest from the damaged vessel which is supplied by other vessels is least severely damaged; tissue intermediate of these extremes shows intermediate damage. Afflicted subjects are administered hsp70 to combat mortality in cells subject to this type of stress.

As noted above, the present invention may be employed to combat restenosis after angioplasty. Angioplasty is a procedure for dilating arteries which are occluded or blocked. In a typical transluminal baloon angioplasty procedure, a catheter which carries an inflatable dilation balloon at the distal end is employed to reshape a partially occluded artery. The balloon is inserted in the deflated condition in the restricted portion of the artery and inflated so that the occluded lumen is reshaped by the dilation balloon to allow better passage of blood. The obstructing material is neither dislocated nor removed from the vessel, but rather pressed against the wall. The wall, in turn, is stretched to accommodate the previously obstructing material. After the lumen has been reshaped, the dilation balloon is deflated and removed. The site of the formed obstruction may, however, become reoccluded when/if the vessel returns to its previous configuration: a phenomenon known as "restenosis." A variety of angioplasty procedures and instruments are known. See, e.g., U.S. Pat. Nos. 4,838,269 and 4,794,928 (the disclosures of which are to be incorporated herein by reference). A subject in need of treatment to prevent restenosis (i.e., either during angioplasty or after angioplasty prior to the onset of restenosis) may be treated by administering hsp70 to the lumen of the vessel which has been reshaped (e.g., by intraveneous injection or intraarterial injection). Any administration which places hsp70 into the bloodstream of the subject or at the site of treatment is suitable, but preferably the administration procedure will direct the hsp70 to the particular site of the angioplasty (i.e., the vessel wall which has been reshaped). For example, the hsp70 may be applied directly to the site of treatment by means of a sweating baloon catheter (i.e., an angioplasty balloon which is perforated so as to administer hsp70 through the perforations to the arterial cell wall during angioplasty).

Skin tissue under stress due to wounds, burns, ulcers, infections, and other types of traumatic injury may be treated by the method of the present invention. For such purposes HSP70 may be administered by topical application to the skin in the form of a salve of cream to enhance repair and healing of the tissue. Tissues may also be under stess due to chemotherapeutic treatment, as in cancer chemotherapy. In such cases HSP70 may be administered subsequent to the chemotherapeutic treatment as a "rescue" agent.

Hsp70 is a member of the heat shock protein (or "hsp") family, which are produced when cells or organisms are exposed to elevated temperatures. This response has been observed in essentially all organisms to date. See generally S. Lindquist, The Heat-Shock Response, *Ann. Rev. Biochem.* 55, 1151 (1986). For example, hsp70 has been found in plants. See, e.g., J. Marshall et al., *Proc. Natl. Acad. Sci. USA* 87, 374 (1990). The hsp70 group is the most highly conserved member of the hsp family. For example, the human protein is 73% identical to the Drosophila protein and is 50% identical to the corresponding *Escherichia coli* protein dnaK. See B. Bukau et al., DnaK and GroE Proteins Play Roles in *E. coli* Metabolism at Low and Intermediate Temperatures as Well as at High Temperatures, in *Stress-Induced Proteins,* 27 (1989)(published by Alan R. Liss, Inc.).

Many of the differences are merely homologous substitutions, and there are regions of homology which those in the field consider to be extraordinary. S. Lindquist, supra at 1155–56.

Within some species, the term "hsp70" itself denotes a family of closely related proteins, all found in that species. In *Saccharomyces cerevisiae,* strains bearing certain hsp70 mutations are nonviable, but viability can be restored by altering the transcriptional regulation of the remaining genes. See E. Craig et al., Complex Regulation of Three Heat Inducible hsp70 Related Genes in *Saccharomyces cerevisiae,* in *Stress-Induced Proteins,* 51 (1989). In view of the biological interchangeability and homology, any member of the hsp70 family within a species is contemplated as useful in practicing the present invention.

As to species of origin, in view of the highly conserved nature of the hsp70 family among broadly divergent species, hsp70 from any species of origin is contemplated as useful in practicing the present invention (numerous references to hsp70 are set forth above, the disclosures of which are to be incorporated herein by reference). Thus, animal, plant (e.g., *Pisum sativum*), and bacterial hsp70 are all contemplated as useful for treating cells or tissue of any origin in practicing the present invention. It is, nevertheless, contemplated that an hsp70 of related origin to the cell or tissue being treated will be preferred for practicing the present invention. For example, plant hsp70 is contemplated as preferred for treating plant cells or tissue, animal hsp70 is contemplated as preferred for treating animal cells or tissue, mammalian hsp70 is contemplated as preferred for treating mammalian cells or tissue, and so on.

The term "HSP 70" is intended to include active fragments, subunits, and artificial analogs thereof. Those regions of the HSP70 molecule which show the greatest structural similarity between different organisms and species are contemplated to be the key sources of its biological activity. Therefore, fragments of the native protein, analogs which contain substitution mutations, deletion mutations, or addition mutations, or even entirely synthetic analogs of HSP70, can be prepared in accordance with known procedures and tested in a routine manner for their ability to increase the metabolic stress tolerance of a sample of tissue or cells using the procedures described herein.

Dose of hsp70 will vary depending on the particular route of administration used. In general, for systemic, local, and in vitro treatments, an overall dose range of from about 0.02 milligrams to about 20 milligrams hsp70 per gram of cells or tissue being treated is contemplated. It is further contemplated that, for local treatments, the maximum doses will be about twenty times greater than the maximum systemic doses.

HSP70 may be administered concurrently or in combination with other therapeutic agents. For example, the HSP70 may be combined with another agent known to protect cells from acute injury. Such agents include anti-oxidants or free radical scavengers such as vitamins C and E and superoxide dismutase when the damaging event works through the production of reactive oxygen molecules. When the mechanism of cell damage involves the influx of extracellular calcium, the other agent might be one which reduces the influx of excess calcium ions (e.g., in brain tissue) such as dextrorphan and MK-801. When the mechanism of damage is myocardial infarction, the other agent might be one that removes the blockage of blood flow to the heart muscle, such as tissue plasminogen activator (TPA) and streptokinase.

Hsp70 may be administered per se or in the form of a pharmaceutically acceptable salt. When used in medicine, the salts of hsp70 should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical formulations, both for veterinary and for human medical use, which comprise hsp70 together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

The formulations include those suitable for oral, rectal, topical, nasal, ophthalmic or parenteral (including subcutaneous, intramuscular and intravenous) administration, all of which may be used as routes of administration for practicing the present invention. Other suitable routes of administration include intrathecal administration directly into spinal fluid (CSF), direct injection onto an arterial surface to prevent re-stenosis, and intraparenchymal injection directly into targeted areas of an organ. Formulations suitable for parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets or lozenges, each containing a predetermined amount of the potentiating agent as a powder or granules; as liposomes containing hsp70; or as a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

HSP may be measured and used as a marker for stress related disease events. Since HSP proteins are induced in cells as a result of stress and since such stressed cells frequently lyse, HSP proteins such as Hsp 70 or fragments thereof are shed in the supernatant of cell cultures and the circulatory system of animals. These proteins may be measured by a number of techniques, including the application of monoclonal antibodies, and provide a marker for stress induced by such events as stroke, myocardial infarction, cancer and other disease states. For example, a blood sample (e.g., in the case of suspected myocardial infraction) or a cerebrospinal fluid sample (e.g., in the case of suspected stroke) may be collected from a patient and contacted to anti-Hsp antibodies in any suitable immunoassay to detect the presence or absence of Hsp proteins or fragments thereof in the sample, the presence of such proteins or protein fragments indicating a stress-related disorder in the patient. Antibodies may be polyclonal or monoclonal, and may be obtained by means known to those skilled in the art. See, e.g.,, W. Huse, Generation of a Large Combinatorial Library of the Immunoglobulin Repertoire in Phage Lambda, 246 Science 1275 (8 Dec. 1989); Kohler and Milstein, 265 Nature 495 (1975). The immunoassay may be a homogeneous or heterogeneous immunoassay procedure. Any suitable procedure may be employed, including radioimmunoassays, immunofluorescence assays, enzyme-linked assays, and the like. See U.S. Pat. Nos. 4,906,562; 4,863,854; and 4,818,682; See also E. Magio, Enzyme-Immunoassay (CRC Press 1980). The assay may be a two-site or "sandwich" assay, as described in U.S. Pat. No. 4,376,110.

The following Examples are provided to illustrate the present invention, and should not be construed as limiting thereof. Temperatures are given in degrees Celsius unless otherwise indicated.

EXAMPLE 1

Effect of hsp70 on Survival of Aortic Cells from Normal and Atherosclerotic Cynomologus Macaques

A. METHODS

1. Materials.

Low calcium (0.2 mM) Hank's balanced salt solution (LC-HBSS) supplemented with essential and nonessential amino acids, penicillin (100 IU/ml), streptomycin (100 μg/ml), and phenol red indicator, and special low calcium Hank's balanced salt solution (SL-HBSS) without amino acids or phenol red, where prepared fresh prior to use in accordance with known techniques. See N. Haley et al., *Lab. Invest.* 37, 287 (1977). Chromatographically purified collagenase and elastase were obtained from Worthington Diagnostics (Freehold, N.J., USA). Soybean trypsin inhibitor (crude) was from Millipore, Inc. (Bedford, Mass., USA). The 4-methylumbeliferyl-2-acetimido-2-deoxy-β-D-glucopyranoside (MW 379.37) substrate for N-acetyl-β-glucosaminidase (NABA) enzyme activity assays was from Koch-Light Laboratories (Coinbright-Bucks, UK). The hsp70 employed was purified from bovine brain essentially according to the procedure of Schlossman et al., 99 J. Cell Biol. 723 (1984). The hsp70 and N27F34 monoclonal antibody were gifts from Dr. Lawrence Hightower (University of Connecticut, Storrs) and Dr. William Welch (University of California, San Francisco), respectively. The horseradish peroxidase-conjugated secondary antibody for Western blot analysis and lactate dehydrogenase, histone H-IIa, and parathyroid hormone for comparison against hsp70 were from Sigma Chemicals (St. Louis, Mo., USA).

2. Induction of Atherosclerosis.

Eight adult male cynomolgus macaques were obtained from Charles River Laboratories, and housed in individual cages. Five animals were fed an atherogenic diet consisting of 1.0 mg cholesterol/kcal, with 40% of calories from butterfat, 38% of calories from carbohydrates, 22% of calories from protein, and 270 ml water/kg, D. Small et al., *J. Clin. Invest.* 73, 590 (1984). Three control animals were fed Purina® Monkey Chow. Monkeys were fed these diets ad libitum for 23–27 months. Periodic plasma lipid profiles were determined as a measure of success in induction of hypercholesterolemia (Table 1).

3. Animal Sacrifice and Cell Isolation.

Animals were anesthetized with 0.2 cc of ketamine HCl and 1.0 cc of sodium pentobarbital (IV). Aortas were removed from the aortic arch to the iliac bifurcation and held in normal saline at 4° C. Adherent adventitia was dissected away and each aorta then opened and laid flat. Aortas were assessed visually for grade of atherosclerosis on a scale of 0 to IV, F. Parker, G. Oglund, *Am. J. Pathol* 48, 197 (1966), and for percent confluency (Table 1). Sections weighing approximately 1.0 g each were dissected and minced to 250 μm squares using a McIlwain tissue chopper (Beckman Instruments, Fullerton, Calif., USA). The minced material was placed in 1.0 ml of LC-HBSS per 100 mg of tissue, which contained 600 U/ml collagenase, 5 U/ml elastase, and 1 mg/ml soybean trypsin inhibitor. The digestion mix was incubated at 37° C., adding sodium carbonate as needed to maintain neutrality, and shaking in a Dubnoff Metbolic incubator (Fisher, Pittsburgh, Pa., USA). Released cells were collected every 30 minutes, separated from the enzyme mixture, washed twice with SL-HBSS for 6 minutes at 3000 rpm, and suspended in 2.0 ml of SL-HBSS at 4° C. until all cells were harvested. Individual harvests were pooled, the cell concentrations determined, and the isolate diluted to $10^6$ cells/ml with SL-HBSS. The final diluted isolate was held at 4° C. prior to and after a treatment regimen.

4. Confirmation and Characterization of hsp70.

Bovine brain hsp70 was received as a solution of 10 μg/μl in 20 mM HEPES buffer, pH 7.0 and routinely stored at −30° C. The composition was confirmed using Western blot analysis. Samples of protein were separated on 10% polyacrylamide gel under reducing conditions, blotted to nitrocellulose, and reacted with N27F34, a murine monoclonal antibody specific to the 73 kD constituitive and 72 kD inducible hsps. The secondary antibody was horseradish peroxidase-conjugated, rabbit anti-mouse anti-IgG. Final staining was with diaminobenzidine/hydrogen peroxide in Tris buffer, pH 7.2. Relative densities of the identified protein bands were determined using an Ultroscan XL laser densitometer (LKB, Rockville, Md. USA).

5. Induced Stress of Cell Isolates.

Normal and diseased arterial cell isolates were tested for changes in viability and structure-linked latency of lysosomal enzymes, in response to extended stress. Samples of 0.2 ml of cell isolates were placed in sealed 1 ml Eppendorf tubes with 0.01 ml of SL-HBSS with or without hsp70 added. Dose-response for hsp70 was determined using cells exposed to 37° C. for 20 hours, with and without 2, 5, 10, or 100 ng hsp70 added per $10^3$ cells. To determine responses following thermal-induced stress, cells were exposed to 23°, 37°, or 45° C. for 20 hours, with or without 10 ng of hsp70 added per $10^3$ cells. Comparative studies for nonspecific changes due to exogenous protein were performed at 37° C. using lactate dehydrogenase, histone H-IIa, and parathyroid hormone, at normal and ten times normal physiological concentrations.

6. Assessment of Cell Viability and Lysosomal Membrane Integrity

Cell viability was determined immediately following the 20 hour test period using 0.4% Trypan blue dye exclusion. Each stored cell suspension was sampled in quadruplicate and examined individually by two investigators. Intact cells versus cell lysis also were noted. Structure-linked latency of lysosomal N-acetyl-β-glucosaminidase (NABA) was calculated as representative of lysosomal membrane integrity. Free and total NABA activities were determined fluorometrically as described previously. See P. Berberian, S. Fowler, *Exp. Mol. Pathol.* 30, 27 (1979). Briefly, samples of 0.1 ml of experimental aortic cells were suitably diluted in SL-HBSS, and incubated 90 minutes at 37° C. with 0.1 ml of 0.50mM 4-methylumbelliferone substrate in 250 mM sucrose containing 100 mM sodium citrate buffer, pH 4.8, with (total activity) or without (free activity) 0.1% Triton X-100. Structure-linked latency of lysosomal enzymes was defined by the difference between total and free NABA activity, and was expressed as a percent of total activity, J. Berthet et al., *Biochem. J.* 50, 182 (1952).

7. Statistical Methods

The results were analyzed for differences in cell viability and structure-linked lysosomal enzyme latency using repeated measures ANOVA. Samples were compared for effects of disease versus control aortic cells, dosage of heat shock protein added, and temperature during test incubation. The interrelationship of viability and latency was tested using standard linear regression.

B. RESULTS

1. Dietary Induction of Atherosclerosis

The atherogenic diet induced hypercholesterolemia with subsequent plaque formation, as shown in Table 1. Light and electron microscopic examination of cell isolates from diseased aortas contained a large proportion of lipid-filled foam cells and lipid-enriched smooth muscle cells as well as normal smooth muscle cells. Normal aortas exhibited no lesions, and their respective cell isolates contained primarily normal smooth muscle cells.

TABLE 1

Monkey Blood Lipid Values and Atherosclerosis Grade

| Monkey No. | Atherogenic Diet | Chol.[1] | HDL[1] | TG[1] | Grade[2] | Confluency % |
|---|---|---|---|---|---|---|
| 1 | Yes | 778 | 15 | 16 | II–III | 70 |
| 2 | Yes | 572 | 33 | 21 | II | 30 |
| 3 | Yes | 672 | 40 | 92 | III | 100 |
| 4 | No | 112 | 65 | 23 | 0 | — |
| 5 | No | 142 | 66 | 28 | 0 | — |
| 6 | No | 183 | 100 | 27 | 0 | — |

[1]Plasma values are from pre-sacrifice, fasted animals, and are expressed as mg/dl. Chol. = total plasma cholesterol; HDL = total plasma high-density lipoproteins, TG = total plasma triglycerides.
[2]Grade: 0 = No lesions; II = Minimally raised atheromatous lesions; III = Significantly raised atheromatous lesions, with fibrosis.

2. Characterization of hsp70

Western blot analysis of the purified hsp70 used in these studies yielded two immunoreactive bands, corresponding to the 73 kD constituitive (estimated 70% of total reactive protein) and 72 kD induced (estimated 30% of total reactive protein) forms of hsp.

3. Effect of Thermal-Induced Stress Upon Viability and Lysosomal Membrane Integrity of Isolated Cells Since data analyses using repeated measures ANOVA did not show any significant differences in test responses between cell isolates from normal and diseased animals, the isolates were considered similar in their response, and the data discussed pooled for analysis ($n=6$). A linear regression of structure-linked latency of lysosomal enzymes (i.e., lysosomal membrane integrity) versus viability for control (No hsp70) aortic cell isolates ($n=23$) showed lysosomal membrane integrity and viability were well correlated ($r=0.85$), regardless of incubation temperature. Furthermore, viability and lysosomal membrane integrity of control samples both declined significantly ($p<0.0005$ and $<0.004$, respectively) as incubation temperature rose. Treatment with hsp70, however, produced disproportionate effects upon these two parameters.

The response of isolated cells at 37° C. for 20 hours to hsp70 showed a significant increase ($p<0.05$) in viability at or above 10 ng hsp70 per $10^3$ cells, compared to cells without added hsp. No change in viability occurred even with a ten-fold increase in the dose to 100 ng hsp70 per $10^3$ cells. Temperature-response studies showed 10 ng hsp70 per $10^3$ cells increased cell viability ($p<0.05$) after storage for 20 hours at all three temperatures tested, with the greatest effect present at 37° C. Based on these results, the optimum temperature for resolution of long-term (i.e., 20 hours) effects of added hsp was 37° C. In contrast, no effect of hsp70 on lysosomal membrane integrity was evident for the doses of added hsp or temperature range tested. Studies at 37° C. of three control proteins tested individually for non-specific exogenous effects each failed to show a maintenance of viability or lysosomal membrane integrity, at either normal or ten times normal physiological concentrations.

C. DISCUSSION

The data presented here showed that exogenous hsp70 can enhance arterial cell survival. The use of a relatively long test period at a physiological temperature as the stress parameter appears unique to the study. Previous hsp studies have used brief periods (15-90 minutes) at relatively high temperatures (42°-45°) to stress cells or animals, M. Schlesinger et al., Cold Spring Harbor Laboratory, 1982; M. Pardue et al., Alan R. Liss, Inc. (1989). In contrast, atherosclerotic plaques represent a system of chronic, multiple stresses. To more closely parallel these conditions, and especially those found in the necrotic core of a plaque, the present studies stressed cells by a combination of enzymatic cell release, hypoxia, low amino acid levels, and longer incubation periods.

Statistical differences were not observed in the test responses between normal and diseased arterial cell isolates. This may reflect the limited population size of this study, and/or the limited extent of atherosclerosis, i.e., the lack of arterionecrosis in these animals. Additionally, the procedure employed for cell release and the test conditions applied in this study may have caused a maximal hsp response for both normal and diseased cell isolates, masking differences in hsp responses present in vivo. The large proportion of normal smooth muscle cells found in even the most diseased aortas might also have a masking effect. The lack of differences could also reflect the potential point of action for exogenous hsp. If hsp affects viability via plasmalemma effector sites whose composition or number do not change during atherogenesis, the reaction cells to exogenous hsp would be the same regardless of their level of lipid load. Thus, the results given here indicate a possible common pathway for the effect of exogenous hsp on arterial cells.

Viability and lysosomal membrane integrity are well correlated normally over a range of temperatures, but have discordant responses to exogenous hsp70. The positive effect of added hsp70 on viability of cell isolates was initiated by as little as 10 ng/$10^3$ cells and, once a significant effect was obtained, a ten fold increase in hsp concentration failed to induce further changes in cell viability. This increase occurred over a range of temperatures, but was most significant at 37° C., possibly due to a maximal activation of degradative enzymes in the cells under study at this temperature.

In contrast to cellular viability, lysosomal membrane integrity was not significantly changed by exogenous hsp70. This observation may reflect a time-dependent factor yet to be determined. A decline in structure-linked lysosomal latency with temperature occurred for samples both with and without added hsp. If lysosomal NABA latency is an earlier marker than viability for membrane integrity in this system, measurements at time points before 20 hours may reveal changes in latency across all temperatures which are comparable to later changes in viability. To address this, time response studies are currently underway. Alternately, hsp70 may affect cell viability by a mechanism more specific than general cell membrane stabilization. If so, structure-linked lysosomal latency may be affected independently of viability or be unaffected by exogenous hsps.

EXAMPLE 2

Protection of Nerve Tissue with HSP70

This experiment was conducted to demonstrate the use of hsp70 to protect nerve tissue against damage using light damage in the rat retina as a model system. Procedures were essentially as described in M. Barbe et al., *Science* 241, 1817 (1988). hsp70 was as described in connection with Example 1 above.

Two groups of three rats each received an injection into the vitreous chamber of the right eye of a saline solution that contained either 2 μg or 10 μg of purified hsp70. These rats also received in the left eye an injection of the saline solution alone to control for any effect the injection itself might have. A third group of two rats were not injected and served as untreated controls. All three groups were exposed to 175-200 foot-candles of fluorescent light beginning four hours after the injections and continuing for 24 hours. Two weeks after the light exposure, the eyes of each rat were prepared for routine histology and the number of surviving photoreceptors in each eye determined by standard techniques. The difference in surviving photoreceptors between the right and left retinas was then calculated. A protective effect of the injected hsp70 is indicated when that difference is significantly greater than zero. On the other hand, if there was no effect of the injected hsp70, the loss of photoreceptors from the right and left eyes should average out to the same, giving a right-left difference that is not significantly different from zero.

Based on a number of statistical comparisons, the group that received the 10 ug dose of Hsp70 showed significant protection of the retinal photoreceptors against the light damage ($p<0.05$), with the right eye having about 36% more photoreceptors than the left eye. The group that received the 2 μg dose of Hsp70 showed a trend in the same direction as the higher dose group, but it did not attain statistical significance with the small number of subjects tested.

The foregoing examples are illustrative of the present invention, and are not to be construed as limiting thereof. The invention is defined by the following claims, with equivalents of the claims to be included therein.

That which is claimed is:

1. A method of combatting mortality in a tissue under stress, which stress induces an endogenous HSP70 response in said tissue, said method comprising contacting exogenous HSP70 to the tissue in an amount effective to enhance the survival of cells in that tissue.

2. A method according to claim 1, wherein said hsp70 is animal hsp70.

3. A method according to claim 1, wherein said hsp70 is mammalian hsp70.

4. A method according to claim 1, wherein said tissue is mammalian tissue.

5. A method according to claim 1, wherein said tissue is arterial tissue.

6. A method according to claim 1, wherein said tissue is nerve tissue.

7. A method according to claim 1, wherein said tissue is maintained in vitro and said contacting step is carried out in vitro.

8. A method of combating atherosclerosis in a human or animal subject, comprising administering to the subject exogenous hsp70 in an amount effective to reduce necrosis in arterial plaques residing in the subject.

9. A method according to claim 8, wherein said administering step is carried out by intravenous injection.

10. A method of combating arterial restenosis after angioplasty in a human or animal subject, comprising administering to arterial tissue residing in the subject exogenous hsp70 in a restenosis-combating amount.

11. A method of combatting mortality in nerve tissue under stress, which stress induces an endogenous HSP70 response in said tissue, said method comprising contacting exogenous HSP70 to the tissue in an amount effective to enhance the survival of cells in that tissue.

12. A method according to claim 11, wherein said stress is anoxic stress arising from a stroke.

13. A method according to claim 11, wherein said hsp70 is animal hsp70.

14. A method of supplementing the endogenous HSP70 response of the cells of a tissue under stress comprising contacting exogenous HSP70 to the tissue in an amount effective to elevate the concentration of HSP70 therein and thereby enhance the survival of the cells in that tissue.

15. A method according to claim 14, wherein said tissue is mammalian tissue.

16. A method according to claim 14, wherein said HSP70 is mammalian HSP70.

17. A method of combatting mortality in tissue of the eye under stress, which stress induces an endogenous HSP70 response in said tissue, comprising contacting exogenous HSP70 to the eye tissue locally in an amount effective to enhance the survival of cells in that tissue.

18. A method according to claim 17, wherein said eye tissue is human eye tissue.

19. A method according to claim 17, wherein said stress is mechanically induced.

20. A method according to claim 17, wherein said stress is light induced.

21. A method according to claim 17, wherein said stress is chemically induced.

22. A method according to claim 17, wherein contacting step comprises topically contacting said eye tissue with HSP70.

23. A method according to claim 17, wherein said contacting step comprises introducing said HSP70 into the vitreous chamber of the eye.

24. A method according to claim 17, wherein said eye tissue is corneal tissue.

25. A method of supplementing the endogenous HSP70 response of the cells of a mammalian eye under stress comprising contacting locally the eye with an ophthalmic preparation containing exogenous HSP70 in an amount effective to elevate the concentration of HSP70 therein and thereby enhance the survival of the cells in that tissue.

26. A method according to claim 25, wherein said eye tissue is human eye tissue.

27. A method according to claim 25, wherein said stress is mechanically induced.

28. A method according to claim 25, wherein said stress is light induced.

29. A method according to claim 25, wherein said stress is chemically induced.

30. A method according to claim 25, wherein contacting step comprises topically contacting said eye tissue with HSP70.

31. A method according to claim 25, wherein said contacting step comprises introducing said HSP70 into the vitreous chamber of the eye.

32. A method according to claim 25, wherein said eye tissue is corneal tissue.

* * * * *